United States Patent [19]

Shepler et al.

[11] Patent Number: 4,710,840
[45] Date of Patent: Dec. 1, 1987

[54] GENERATING SYSTEM WITH FAULT DETECTION

[75] Inventors: John E. Shepler; Dov Zur, both of Rockford, Ill.

[73] Assignee: Sundstrand Corporation, Rockford, Ill.

[21] Appl. No.: 689,765

[22] Filed: Jan. 8, 1985

[51] Int. Cl.⁴ .............................................. H02H 7/06
[52] U.S. Cl. ....................................... 361/20; 322/59; 322/69; 364/200; 364/900; 365/228
[58] Field of Search ................. 361/20, 21; 322/89, 322/91, 8, 59, 94, 27, 69, 70; 364/200, 900; 365/226, 228

[56] References Cited

U.S. PATENT DOCUMENTS

| | | | |
|---|---|---|---|
| 2,845,593 | 7/1958 | Lowry, Jr. | 322/25 |
| 2,885,569 | 6/1959 | Schuh et al. | 307/87 |
| 2,977,511 | 3/1961 | Reeder et al. | 317/54 |
| 3,248,608 | 4/1966 | Farkas et al. | 317/13 |
| 3,351,812 | 11/1967 | Cutler et al. | 317/13 |
| 3,471,749 | 10/1969 | Harris | 317/23 |
| 3,705,331 | 12/1972 | South et al. | 322/25 |
| 3,976,917 | 8/1976 | Fork | 371/13 R |
| 4,155,107 | 5/1979 | Osborne et al. | 361/20 |
| 4,187,525 | 2/1980 | Nagura et al. | 361/42 |
| 4,245,182 | 1/1981 | Aotsu et al. | 322/20 |
| 4,288,736 | 9/1981 | Wright | 361/21 |
| 4,322,630 | 3/1982 | Mezera et al. | 290/40 |
| 4,326,159 | 4/1982 | Aotsu et al. | 322/19 |
| 4,327,410 | 4/1982 | Patel et al. | 365/228 |
| 4,377,784 | 3/1983 | Saito et al. | 324/158 |
| 4,486,801 | 12/1984 | Jackovich et al. | 322/59 |
| 4,523,295 | 6/1985 | Zato | 364/900 |

Primary Examiner—A. D. Pellinen
Assistant Examiner—Jeffrey A. Gaffin
Attorney, Agent, or Firm—Wood, Dalton, Phillips, Mason & Rowe

[57] ABSTRACT

"Doorbelling" in a generating system including a fault detecting circuit is prevented without the use of auxiliary power supply for a generator control unit. The generating system includes a permanent magnet generator (14) driving an exciter winding (18) and a relay (26) is utilized for interconnecting the two. Control of the relay (26) is exercised by a microcomputer (32) including a non-volatile memory (48) and programmed to remember the occurrence of a fault and thereafter prevent the relay (26) from cyclically opening and closing in response to power changes occurring as a result of connection and disconnection of the exciter winding (18) from the permanent magnet generator (14).

8 Claims, 3 Drawing Figures

GENERATING SYSTEM WITH FAULT DETECTION

FIELD OF THE INVENTION

This invention relates to a generating system, and more particularly, to a generating system provided with means for detecting the existence of a fault therein and for responding to such detection to disconnect parts of the system to prevent the damage that would be occasioned by the existence of a fault.

BACKGROUND OF THE INVENTION

When a fault develops in a generating system, the resulting excessive load on the system caused by the fault can cause grave damage to the system as a result of overheating or other associated problems. While the problems associated with the development of faults are of concern in almost all generating systems, they may be particularly acute in the generating systems employed in aircraft having high electrical power requirements. In particular, aircraft generating systems are quite expensive in relation to their generating capacity and if damage is sustained as a result of a fault, it is commensurately more expensive to repair. Moreover, in many instances, the economical operation of aircraft depends upon a high rate of utilization of such aircraft. Consequently, excessive down time of the aircraft for repair of fault caused damage to a generating system may severely impede efficient use of such aircraft.

Consequently, such power systems must be provided with control units that are capable of detecting faults and in turn, prevent the fault condition from causing the generator to cycle on and off continuously, a phenomenon sometimes termed "doorbelling".

A particularly troublesome fault condition in generating systems is that occassioned by a short circuit to electrical ground on the supply side of the generator exciter field winding. In a typical generating system, a permanent magnet generator provides power for the control unit and to a rectifier bridge which in turn conveys power to the exciter field winding of the main generator. Typically, the control unit operates an electrically held relay which opens contacts in the exciter field supply circuit when power is removed from the control unit or when a fault detector determines that a fault condition exists. When the relay is closed, power is supplied to the exciter field winding. Conversely, when the relay is opened, power is removed from the exciter field winding.

Under normal conditions, the control unit will cause the relay to close to connect the exciter field winding into the circuit. Should a fault occur, the resulting load causes the permanent magnet generator to be extremely heavily loaded and its voltage output is accordingly greatly reduced. The permanent magnet generator will not develop sufficient voltage to power the control unit and as a consequence, it cannot continue to command the relay to maintain a closed condition and the relay opens.

When the relay opens, the heavy loading on the permanent magnet generator ceases to exist and the permanent magnet generator then provides a full voltage output. At this point, the control unit receives enough voltage to resume operation and causes the relay to close. As a consequence, the voltage at the output of the permanent magnet generator again becomes greatly reduced because of the heavy loading caused by the reconnected fault. Sufficient voltage to power the control unit is again lost and the relay will again open.

This continuous cycling will occur indefinitely until there is manual intervention.

To avoid this problem, in some prior instances, an auxiliary source of power whose voltage is independent of the output of the permanent magnet generator is utilized to provide power to the control unit. When such is used, when the control unit opens the relay in response to the detection of a fault, the relay will remain open so long as the control unit is powered by the auxiliary source of power and is unaffected by the immediate increase in output voltage at the permanent magnet generator upon disconnection of the fault therefrom.

While this approach represents a solution to doorbelling, it requires the presence of an auxiliary source of power; and such may not be readily available, or available at all in various systems.

The present invention is directed to overcoming one or more of the above problems.

SUMMARY OF THE INVENTION

It is the principal object of the invention to provide a new and improved fault detection system for use in generating systems. More specifically, it is an object of the invention to provide a new and improved fault detection system to eliminate so-called "doorbelling" in electrical generating systems. It is a further object of the invention to provide such a fault detection system which does not require an auxiliary source of power.

An exemplary embodiment of the invention achieves the foregoing objects in a fault protection control circuit for use in a generating system including a permanent magnet generator for providing electrical power to an exciter. The fault protection control circuit includes a normally open, electrically controlled switch adapted to be electrically disposed between a permanent magnet generator and an exciter for controlling the provision of electrical power from the former to the latter. The switch is adapted to be powered by the permanent magnet generator. An electrical computing circuit is provided and is adapted to be connected to the permanent magnet generator independently of the switch and to be powered thereby. The computing circuit operates to close the switch. The computing circuit is incapable of operation on the electrical power received from the permanent magnet generator when it is heavily electrically loaded as when a fault in the generating system occurs.

The system includes a memory device whose state is unaffected by the presence or absence of electrical power and which may be altered by operation of the computing circuit. The memory is set to a particular state at the beginning of a generating cycle by the computing circuit and is reset by the computing circuit upon normal conclusion of the generating cycle. The memory remains set upon the interruption of a generating cycle by a fault. The computing circuit, following an interrupting of a generating cycle, checks the memory for the particular state and, in response thereto, operates not to close the switch. In the absence of the particular state, the computing circuit closes the switch.

In a highly preferred embodiment, the computing circuit is a microprocessor and the memory is a non-volatile memory.

In the best mode of the invention, the memory is an electrically eraseable, programmable read only memory.

According to the invention, the computing circuit writes the particular state in the memory at the initiation of a generating cycle and reads the memory at the initiation of a subsequent generating cycle including one being initiated as a result of an interruption of the preceding generating cycle.

The system may include manual means for erasing the information from the memory.

The fault detection system is included with a generating system operated by a prime mover. The computing circuit is adapted to erase a particular state from the memory in response to a shut-down of the prime mover.

Other objects and advantages will become apparent from the following specification taken in connection with the accompanying drawings.

DESCRIPTION OF THE PREFERRED EMBODIMENT

Figure 1:
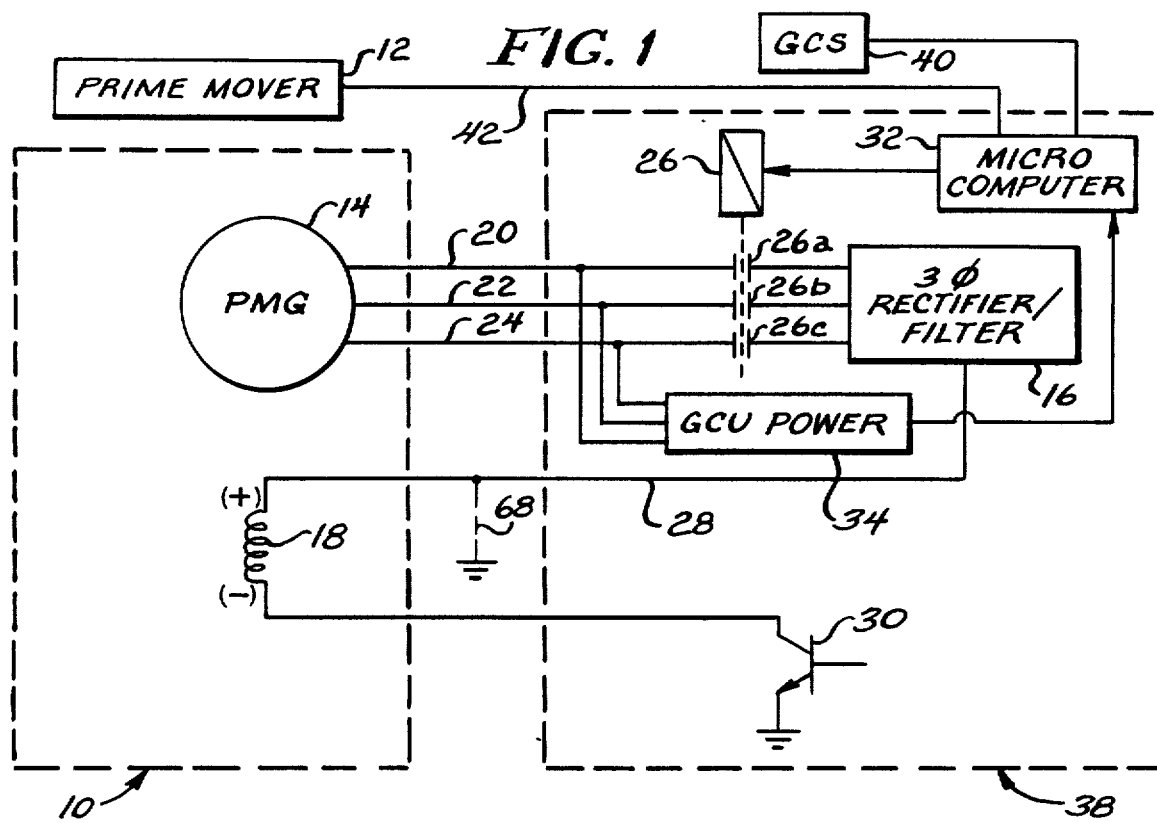
FIG. 1 is a schematic of an electrical generating system embodying the invention.

An exemplary embodiment of the invention is illustrated in the drawings and with reference to FIG. 1 is seen to include a generating system, generally designated 10.

The generating system is driven by a prime mover shown schematically at 12 as, for example, an aircraft engine.

In the usual case, the generating system 10 will be of the so-called brushless variety. Typically, such a generating system will include a permanent magnet generator 14 and in the usual case the same will provide a three phase alternating current output. The output of the permanent magnet generator 14 is rectified by a three phase full wave rectifier bridge 16 and the resulting direct current provided to the field winding 18 of an exciter. The exciter in turn will provide alternating current, usually three phase, to a rotating rectifying device (not shown) which in turn provides direct current to the main field winding of a main generator rotor (not shown). A stator forming part of the main generator provides power to electrical components requiring it.

The permanent magnet generator 14 is connected to the rectifier 16 by three lines 20, 22, 24, one for each phase. The lines 20, 22 and 24 respectively include electrical contacts 26a, 26b, and 26c of a relay 26. The relay 26 is of the normally open variety and acts as electrically operated switch controlling the flow of electrical energy from a permanent magnet generator to the rectifier bridge 16 and then to the exciter field winding 18. The latter is connected to the rectifier bridge 16 by a line 28 and to ground via a field regulator transistor 30 which controls the flow of power through the exciter winding 18 in a conventional fashion.

The relay 26 is driven by a computing circuit or microcomputer 32. The microcomputer 32 is powered by a generator control unit power unit 34 which in turn is connected to the output of the permanent magnet generator 14, that is, to the lines 20, 22 and 24, at a location between the permanent magnet generator 14 and the contacts 26a, 26b and 26c. Consequently, the power unit 34 is powered by the permanent magnet generator regardless of whether the relay 26 is operated to close the contact 26a, 26b, and 26c.

The relay 26, microcomputer 32, the rectifier bridge 16 and the power unit 34 along with the field regulator transistor 30 make up a generator control unit, generally designated 38.

The generator control unit 38 may receive inputs of various sorts. For the purposes of the present invention, two are of concern. A first is a manual input from a generator control switch 40 which is directed to the microcomputer 32. A second is an input from the prime mover 12 on a line 42 which is likewise directed to the microcomputer 32.

The manual switch 40 may be operated in a variety of ways. For example, it may be utilized to override the fault detection and protection system of the present invention. It might also be utilized as a control to prevent the system from being cycled without manual actuation.

The input on the line 42 from the prime mover 12 may be utilized as a signal indicative of whether the prime mover 12 is in operation, i.e., running or shut down, for purposes to be seen.

Figure 2:
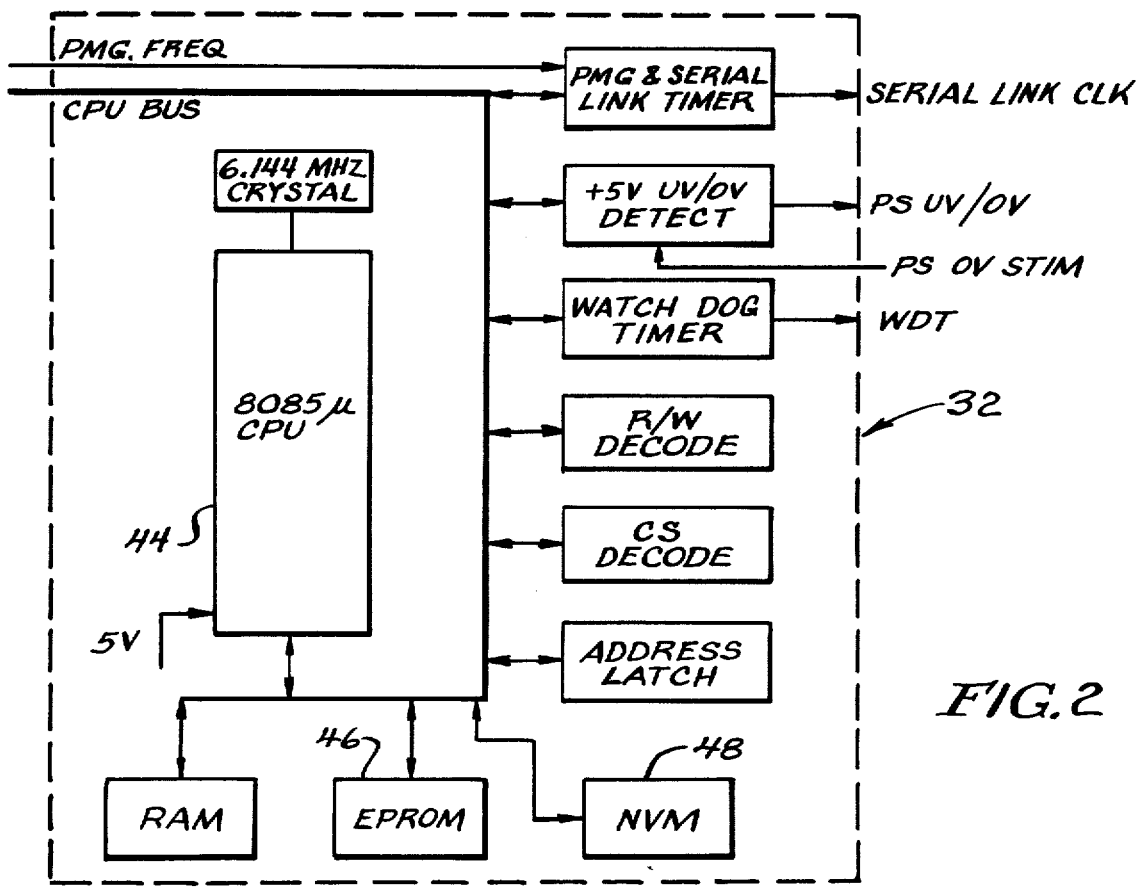
FIG. 2 is a block diagram of a microprocessor or microcomputer that may be used as part of the invention.

The microcomputer 32 is illustrated in block form in FIG. 2 and is based about a central processing unit 44 such as an Am8085A 8-bit central processing unit available from Advanced Micro Devices. In the usual case, the central processing unit 44 will be performing a number of computational routines necessary for the control of the generating system 10 in addition to those involved with fault detection and a number of the functions schematically illustrated are utilized in connection with such routines. For the purpose of the present invention, it is sufficient to note that the microcomputer 32 includes an EPROM unit 46 in which the program relative to fault detection and operation may be stored and a non-volatile memory 48 for purposes to be seen. As used herein, the term non-volatile memory means a memory device whose memory state may be changed by an appropriate signal provided to it by some component of the system most typically the central processing unit 44 in the preferred embodiment. At the same time, a non-volatile memory cannot have its memory state changed by an interruption of its power supply.

Those skilled in the art will readily recognize that a variety of devices, both mechanical and electrical can be used as a non-volatile memory 48. In the preferred embodiment, however, it is preferred to employ an electrically eraseable programmable read only memory as the non-volatile memory 48 as, for example, an X2804A electrically eraseable, programmable read only memory available from Xicor. The manner in which the non-volatile memory 48 is associated with the central processing unit 44 is achieved through conventional techniques and forms no part of the present invention.

Figure 3:
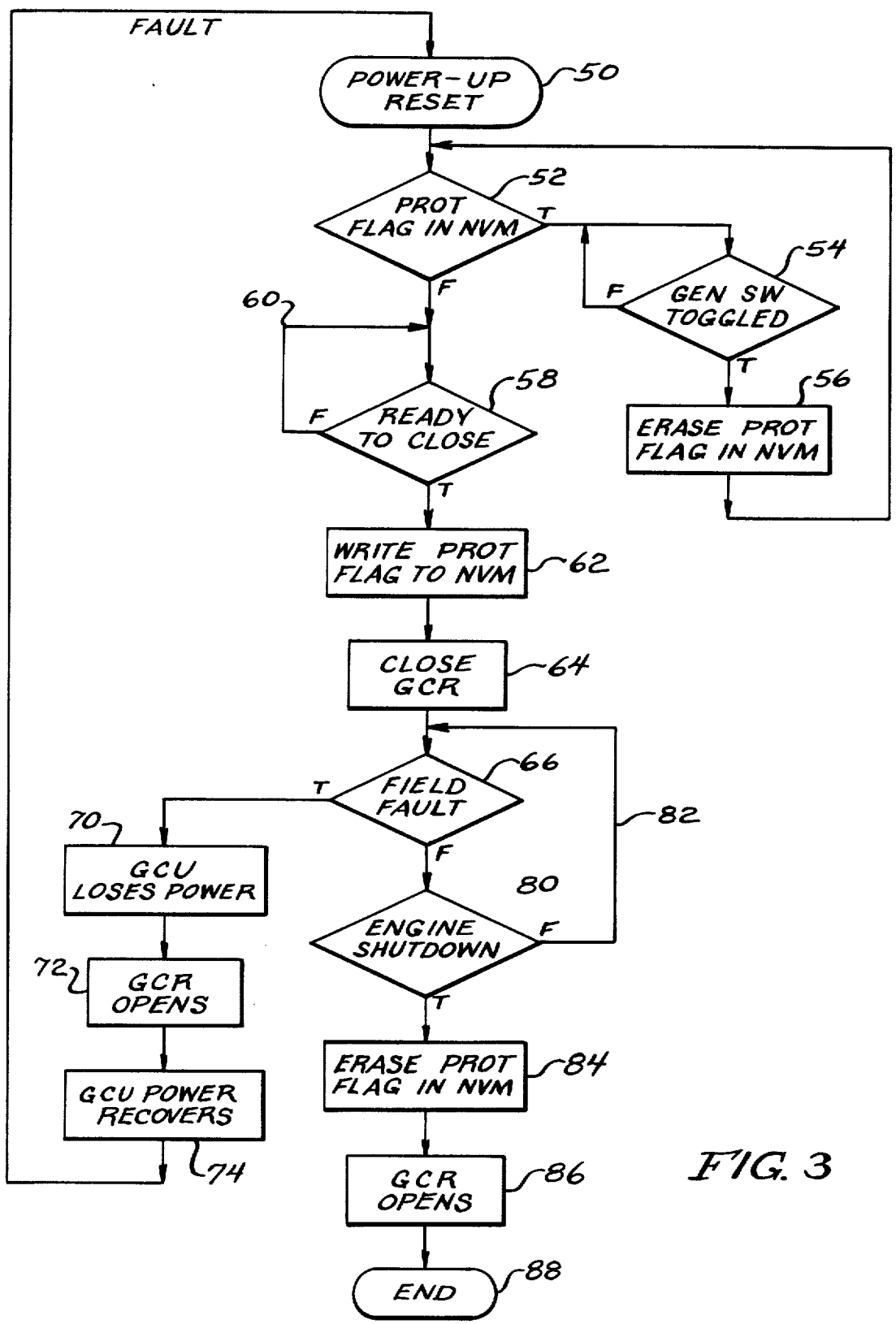
FIG. 3 is a flow diagram of a program routine for the microcomputer which implements the invention.

To achieve fault detection and protection according to the invention, the microcomputer 32 is programmed with the routine illustrated in flow chart form in FIG. 3. Upon initiation of a generating cycle, whether an intentionally initiated generating cycle or in a start-up following an interruption as for example, due to the presence of a fault, the program requires a power up reset routine 50 to be performed as is customary. Upon the completion of the operation designated by the block 50, the non-volatile memory 48 is read to determine whether a protection flag, that is, a particular state of the non-volatile memory, exists therein as shown at block 52. If a flag exists, the program branches to determine whether the generator control switch 40 has been toggled as indicated at block 54. Where the toggling of the switch 40 is such as to call for override of the protection program, if the switch has been toggled, as shown at block 56, the central processing unit 44 is directed to erase the protection flag in the non-volatile memory 48 and execute the lobp illustrated. Conversely, if the switch 40 has not been toggled, the program repetitively cycles in the closed loop illustrated until such toggling of the switch 40 occurs.

If no protection flag has been written in the non-volatile memory 48, the program proceeds to block 58 where an inquiry is made as to whether all other system parameters are such as to ready the system for operation. If not, a closed loop 60 is repetitively followed until the system is ready for operation.

Upon that occurrence, the system then writes a protection flag in the non-volatile memory 48 as shown by block 62. Following such writing, the system operates to energize the relay 26 and close the contacts 26a, 26b and 26c as shown by block 64. This, of course, connects the permanent magnet generator 14 to the exciter field winding 18.

After the relay 26 has been energized, the system proceeds to a block 66 which is indicative of the presence or absence of a fault in the field circuit for the exciter winding 18. Such a fault is shown schematically as a broken line 68 to ground in FIG. 1.

In the event such a fault exists, the extremely high loading placed on the permanent magnet generator 14 will cause its output voltage to drop which in turn will cause a drastic decrease in power to the generator control unit power unit 34 as indicated by the block 70 in FIG. 3. Because of this, the power unit 34 cannot supply power to the microcomputer 32 and the inability of the latter to function without power releases the relay 26 allowing the contacts 26a, 26b and 26c to revert to their normally open condition. This is illustrated at block 72 in FIG. 3.

With the relay contacts 26a, 26b and 26c now open, the permanent magnet generator 14 is disconnected from the fault 68 and no longer is heavily loaded. Its voltage will accordingly increase and the power unit 34 is again able to supply normal operating voltage to the microcomputer 32. This is illustrated at block 74 in FIG. 3.

At this point, the power up reset routine 50 is repeated and following that, the non-volatile memory 48 is read as illustrated in block 52. Because the loop just traced included the writing of the protection flag in the non-volatile memory with no erasure of the same coupled with the fact that the non-volatile memory 48 will retain its memory state even in the absence of power, such as caused by the interruption due to the existence of a fault, the program will branch to the loop including the blocks 54 and 56 will remain there until such time as manually commanded by operation of the switch 40 to erase the protection flag. Accordingly, the relay 26 cannot be re-energized by the microcomputer 32 during such an occurrence without manual intervention and the faulted exciter field winding 18 cannot be reconnected to the permanent magnet generator. As a consequence, doorbelling is completely avoided.

In the more normal situation, where a field fault such as represented by the block 66 does not exist, the program will proceed to determine, at block 80, whether the prime mover 12 is still operating. If the prime mover continues to operate, a loop 82 back to the block 66 is executed and such loop will be continually executed so long as a field fault does not exist or the engine is not shut down. Conversely, if the engine is shut down, the program, at block 84, commands the erasure of the protection flag in the non-volatile memory 48 and with the power supply winding down with the prime mover, the relay 26 will be de-energized to open the contacts 26a, 26b and 26c as shown in block 86. This completes the program as shown at block 88.

In this more normal case, it will be seen that the system is made ready for a normal reinitiation when the next generating cycle is started. Specifically, because the protection flag is erased at the time of shutdown, when, after power up and reset at block 50, the program calls for reading the non-volatile member as at block 52, no protection flag will be found therein. The system may then proceed upon such normal startup in the manner outlined above.

From the foregoing, it can be appreciated that a generator control system and fault detection circuit made according to the invention provides fault detection for the generating system while eliminating the possibility of doorbelling. The system is particularly advantageous in that it does not require provision of an auxiliary power supply to operate the generator control unit 38 and the micro computer 32 therein upon the occurrence of a fault which would render the microcomputer 32 incapable of operation due to insufficient power.

We claim:

1. In a generating system, the combination of: a permanent magnet generator characterized by an output whose voltage is inversely affected by its loading;
   an exciter receiving electrical power from said permanent magnet generator and generating a magnetic field, said exciter including a winding;
   an electrically controllable switch selectively connecting or disconnecting said winding to or from said permanent magnet generator and powered by said permanent magnet generator; and
   a fault detector operating said switch including an electrical computing circuit powered by said permanent magnet generator and characterized by inability to operate at low output voltage levels of said permanent magnet generator caused by heavy loading thereof indicative of a fault in said exciter winding and a non-volatile memory in which is written information indicative of the inability of said computing circuit to operate in response to a said low voltage level, said computing circuit, upon restoration to ability to operate in response to an output voltage increase from said low voltage level, reading said memory in response thereto, and controlling said switch to prevent connection of said winding to said permanent magnet generator.

2. The generating system of claim 1 wherein said switch is nonconducting when unpowered by said computing circuit.

3. The generating system of claim 1 wherein said computing circuit writes said information in said memory at the initiation of a generating cycle and reads said memory at the iniitiation of a subsequent generating cycle.

4. The generating system of claim 1 including manual means for erasing said information from said memory.

5. The generating system of claim 1 including a prime mover for said generating system, and said computing circuit erasing said information from said memory in response to shut down of said prime mover.

6. A fault protection control circuit for use in a generating system including a permanent magnet generator for providing electrical power to an exciter and comprising a normally open, electrially controlled switch adapted to be electrically disposed between a permanent magnet generator and an exciter for controlling the provision of electrical power to the latter, said switch being adapted to be powered by such permanent magnet generator;

an electrical computing circuit means adapted to be connected to a permanent magnet generator independently of said switch to be powered thereby and for controlling the closing of said siwtch;

said computing circuit means being incapable of operation on the electrical power received from a permanent magnet generator when it is heavily electrically loaded as when a fault in the generating system occurs;

a memory device whose state is unaffected by the presence or absence of electrical power but which is controlled by operation of said computing circuit means;

said memory device (a) being set to a particular state at the beginning of a generating cycle by said computing circuit means, (b) being reset by said computing circuit means upon the normal conclusion of a generating cycle, and (c) remaining set upon interruption of a generating cycle by a fault;

said computing circuit means, following an interruption of a generating cycle, checking said memory for said particular state and, in response thereto, not closing said switch, and in the absence thereof, closing said switch.

7. The fault protection control circuit of claim 6 wherein said computing circuit is a microporcessor and said memory is an electrically eraseable programmable read only memory.

8. A fault protection control circuit for use in a generating system including a permanent magnet generator for providing electrical power to an exciter and comprising an electrically controlled switch adapted to be electrically disposed between a permannent magnet generator and an exciter for controlling the provision of electrical power to the latter;

an electrical computing circuit means adapted to be connected to a permanent magnet generator independently of said switch to be powered thereby and for operating said switch;

said computing circuit means being incapable of operation on the electric power received from a permanent magnet generator when heavily electrically loaded as when a fault in the generating system occurs;

a non-volatile memory device whose state is unaffected by the presenece or absence of electrical power but which may be read, written or erased by operation of said computing circuit means;

said memory device (a) being set to a particular state at or near the beginning of a generating cycle by writing by said computing circuit means and (b) being reset by being erased by said computing circuit means upon the normal conclusion of a generating cycle;

said computing circuit means, upon receiving power from said permanent magnet generator following an interruption of its power supply from said permanent magnet generator by a fault, reading said memory device for said particular state and, in response thereto, not closing said switch, and in the absence thereof, closing said switch.

* * * * *